(12) United States Patent
Yamaoka et al.

(10) Patent No.: US 8,871,242 B2
(45) Date of Patent: Oct. 28, 2014

(54) BLOOD ANTICOAGULANT MATERIAL, COATING MATERIAL AND INDWELLING DEVICE COMPRISING THE SAME, AND TREATMENT USING BLOOD ANTICOAGULANT MATERIAL

(75) Inventors: Tetsuji Yamaoka, Osaka (JP); Satoshi Kato, Mie (JP); Atsushi Kasai, Kanagawa (JP); Sachiro Kakinoki, Osaka (JP)

(73) Assignee: National Cerebral and Cardiovascular Center, Osaka (JP)

( * ) Notice: Subject to any disclaimer, the term of this patent is extended or adjusted under 35 U.S.C. 154(b) by 585 days.

(21) Appl. No.: 12/515,365

(22) PCT Filed: Nov. 16, 2007

(86) PCT No.: PCT/JP2007/072328
§ 371 (c)(1),
(2), (4) Date: Jul. 16, 2009

(87) PCT Pub. No.: WO2008/059975
PCT Pub. Date: May 22, 2008

(65) Prior Publication Data
US 2010/0030325 A1  Feb. 4, 2010

(30) Foreign Application Priority Data
Nov. 17, 2006 (JP) .................. 2006-312167

(51) Int. Cl.
| | |
|---|---|
| C08G 63/00 | (2006.01) |
| C08G 63/08 | (2006.01) |
| C08G 63/91 | (2006.01) |
| C08G 67/00 | (2006.01) |
| C08G 69/00 | (2006.01) |
| C08L 67/00 | (2006.01) |
| C08L 53/00 | (2006.01) |
| C09D 153/00 | (2006.01) |
| A61L 33/06 | (2006.01) |

(52) U.S. Cl.
CPC ............... A61L 33/068 (2013.01); C08L 53/00 (2013.01); C09D 153/00 (2013.01)
USPC ............ 424/426; 525/415; 528/271; 528/354

(58) Field of Classification Search
None
See application file for complete search history.

(56) References Cited

U.S. PATENT DOCUMENTS

| | | | |
|---|---|---|---|
| 4,189,425 A | 2/1980 | Shanbrom et al. | |
| 4,438,253 A | 3/1984 | Casey et al. | |
| 5,211,878 A | 5/1993 | Reiffenrath et al. | |
| 6,201,072 B1 | 3/2001 | Rathi et al. | |
| 6,211,249 B1 | 4/2001 | Cohn et al. | |
| 8,357,391 B2 * | 1/2013 | Pacetti et al. | 424/426 |
| 2001/0009662 A1 | 7/2001 | Cohn et al. | |
| 2003/0139567 A1* | 7/2003 | Kim et al. | 528/354 |
| 2003/0185787 A1 | 10/2003 | Hubbell et al. | |
| 2004/0076673 A1 | 4/2004 | Bateman et al. | |
| 2006/0034888 A1* | 2/2006 | Pacetti et al. | 424/426 |
| 2006/0036311 A1 | 2/2006 | Nakayama et al. | |
| 2007/0155906 A1* | 7/2007 | Hissink et al. | 525/242 |
| 2007/0218099 A1 | 9/2007 | Kim et al. | |

FOREIGN PATENT DOCUMENTS

| | | | |
|---|---|---|---|
| JP | 63-162725 | 7/1988 | |
| JP | 8 245775 | 9/1996 | |
| JP | 11 255873 | 9/1999 | |
| JP | 11 299901 | 11/1999 | |
| JP | 2004 754 | 1/2004 | |
| WO | 99 02168 | 1/1999 | |
| WO | 99 10022 | 3/1999 | |
| WO | WO 99/18142 | 4/1999 | |
| WO | WO 02/38184 A1 | 5/2002 | |
| WO | 03 080147 | 10/2003 | |
| WO | 03 090807 | 11/2003 | |
| WO | 2004 022150 | 3/2004 | |
| WO | WO 2006/055049 A1 * | 5/2006 | A61L 33/06 |

OTHER PUBLICATIONS

Attached Google NPL search results dated May 9, 2014 (2 pages).*

* cited by examiner

*Primary Examiner* — Jeffrey T Palenik
(74) *Attorney, Agent, or Firm* — Oblon, Spivak, McClelland, Maier & Neustadt, L.L.P.

(57) ABSTRACT

A blood anticoagulant material is provided which has high expandability, reduced influence on living bodies, and can efficiently prevent blood coagulation.

A multiblock copolymer having at least a structural unit represented by Formula (1), a structural unit represented by Formula (2), and a structural unit represented by Formula (3) is used:

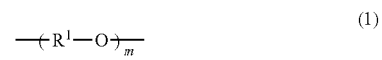

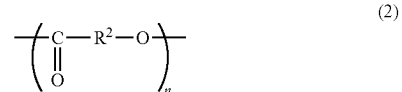

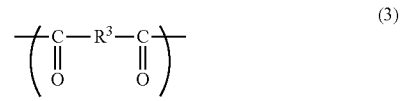

wherein, $R^1$, $R^2$, and $R^3$ in Formulas (1) to (3) each independently represent a divalent organic group, and m and n each independently represent an integer of 2 to 5000.

19 Claims, 2 Drawing Sheets

BLOOD ANTICOAGULANT MATERIAL, COATING MATERIAL AND INDWELLING DEVICE COMPRISING THE SAME, AND TREATMENT USING BLOOD ANTICOAGULANT MATERIAL

TECHNICAL FIELD

The present invention relates to a blood anticoagulant material comprising a multiblock copolymer, a coating material and an indwelling device comprising the blood anticoagulant material, and treatment using the blood anticoagulant material.

BACKGROUND ART

Devices used in medical fields may be indwelled in contact with blood in or on bodies of various living organisms including human beings (hereinafter referred to as "indwelling device") Examples of the indwelling device include stents, catheters, balloons, vascular prostheses, artificial blood vessels, artificial skins, transdermal devices, adhesion-preventing materials, and wound dressings.

Stents are used in treatment of, for example, stenosis and occlusion of body lumens such as blood vessels, bile ducts, tracheas, esophagi, alimentary canal, ureters, and urethras in living bodies. Specifically, the stents are hollow tubes which can be indwelled on lesions such as stenosis and occlusion of body lumens to dilate the lumens and keep them open in treatment of various disorders due to stenosis or occlusion of body lumens such as blood vessels. For example, stents are used in cardiac coronary arteries to prevent restenosis after percutaneous transluminal coronary angioplasty (PTCA). Dwelling such stents in body lumens such as blood vessels after surgery can reduce incidence of acute vascular occlusion and restenosis.

Conventionally, various metals or resins have been used for stents in view of durability and expandability.

These materials, however, have a problem in that blood adheres to surfaces of the stents and clots over time.

To solve such a problem, techniques have been proposed to coat the surfaces of stents with various resins in order to prevent blood coagulation (for example, Patent Documents 1 to 4).

[Patent Document 1] International publication No. WO2003/090807
[Patent Document 2] International publication No. WO2003/080147
[Patent Document 3] U.S. Pat. No. 6,211,249
[Patent Document 4] International publication No. WO99/02168

DISCLOSURE OF INVENTION

Problems to be Solved by the Invention

The techniques disclosed in Patent Documents 1 to 4, however, have the following disadvantages: the resins coated on surfaces of stents have insufficient expandability, contain substances which have undesired influences on living bodies, and can not prevent blood coagulation sufficiently.

In the regenerative medical field, research and development using a carrier (scaffold) such as poly(glycolic acid) have been conducted. In addition, poly(lactic acid) for bone fixation pins, polydioxanone for surgical sutures, and various random copolymers have been widely used in a clinical practice. However, only characteristics such as high mechanical strength, high elasticity, and flexibility have been required for these materials, in addition to bioabsorbability. Accordingly, materials which have excellent compatibility among expandability, high safety to living bodies, and prevention of blood coagulation are not yet known.

For the reasons described above, materials which have high expandability and reduced influence on living bodies, and can efficiently prevent blood coagulation on a surface of an indwelling device such as a stent have been demanded.

The present invention was made in view of this situation. That is, an object of the present invention is to provide a blood anticoagulant material that has high expandability and reduced influence on living bodies, and can efficiently prevent blood coagulation. In addition, an object of the present invention is to provide a coating material and an indwelling device comprising the blood anticoagulant material. Furthermore, an object of the present invention is to provide treatment using a medical device comprising the blood anticoagulant material.

Means for Solving the Problem

To solve the above problems, the inventors have made extensive studies and have found that a blood anticoagulant material which has high expandability and reduced influence on living bodies, and can efficiently prevent blood coagulation can be prepared using a multiblock copolymer having at least structural units represented by Formulas (1) to (3) (polyether block, polyester block, and dicarboxylic acid unit), and accomplished the present invention.

That is, one aspect of the present invention consists in a blood anticoagulant material comprising a multiblock copolymer having at least a structural unit represented by Formula (1), a structural unit represented by Formula (2), and a structural unit represented by Formula (3):

[Chemical formula 1]

[Chemical formula 2]

[Chemical formula 3]

wherein, $R^1$, $R^2$, and $R^3$ each independently represent a divalent organic group, and m and n each independently represent an integer of 2 to 5000 (claim 1).

In this case, the total content of the structural unit represented by Formula (1) and the structural unit represented by Formula (3) in the multiblock copolymer is preferably 5 to 50% by weight (claim 2).

The structural unit represented by Formula (1) is preferably a polyethylene glycol block (claim 3).

The structural unit represented by Formula (2) preferably comprises at least one monomeric component selected from a group consisting of lactic acid, glycolic acid, and caprolactone (claim 4).

R³ in Formula (3) is preferably a divalent hydrocarbon group having ten or less carbon atoms (claim 5).

Another aspect of the present invention consists in a coating material comprising the blood anticoagulant material described above (claim 6).

Another aspect of the present invention consists in an indwelling device of which a surface is coated with the coating material described above (claim 7).

Another aspect of the present invention consists in an indwelling device comprising the blood anticoagulant material described above (claim 8).

In both cases, the indwelling device is preferably a stent (claim 9).

The above blood anticoagulant material is preferably used in order to prevent blood coagulation while an indwelling device is indwelled in a living body (claim 10).

Another aspect of the present invention consists in treatment using a medical device comprising the blood anticoagulant material described above (claim 11).

Advantages

The present invention can provide a blood anticoagulant material which has high expandability and reduced influence on living bodies, and can efficiently prevent blood coagulation.

BEST MODE FOR CARRYING OUT THE INVENTION

The present invention will be described in detail below. It should be noted, however, that the present invention is not limited thereto and various variations can be made within the scope of the invention.

The term "polymer" used herein collectively refers to "homopolymer" (that is, polymer composed of a single monomer) and "copolymer" (that is, polymer composed of different monomers. Copolymer.) unless otherwise specified. Furthermore, the term "polymer" used herein is taken as synonymous with the term "polymer" and "monomer" used herein is taken as synonymous with the term "monomer" unless otherwise specified.

Among the structural units in a polymer or a compound herein, the structural unit derived from a certain monomer compound may be represented by the name of the monomer compound with "unit". For example, the structural unit derived from dicarboxylic acid may be represented by "dicarboxylic acid unit".

Among the structural units in a polymer or a compound herein, the structural unit derived from a certain polymer compound may be represented by the name of the polymer compound with "block". For example, the structural unit derived from polyether may be represented by "polyether block".

Among the structural units in a polymer or a compound herein, (one or more) compounds which can be a material for a certain structural unit may be correctively referred to as the name of the structural unit with "component" instead of "unit" or "block". For example, a compound which can be a material for the dicarboxylic acid unit may be correctively referred to as "dicarboxylic acid component", and a compound which can be a material for the polyether block may be correctively referred to as "polyether component".

The blood anticoagulant material of the present invention comprises a specific multiblock copolymer. This specific multiblock copolymer (hereinafter optionally referred to as "the copolymer of the present invention") will be describe below, followed by the description of the blood anticoagulant material of the present invention, and then the indwelling device of the present invention.

[I. Multiblock Copolymer]

The copolymer of the present invention is a multiblock copolymer having at least a structural unit represented by Formula (1) (hereinafter optionally referred to as "the structural unit (1)"), a structural unit represented by Formula (2) (hereinafter optionally referred to as "the structural unit (2)"), and a structural unit represented by Formula (3) (hereinafter optionally referred to as "the structural unit (3)"):

[Chemical formula 4]

(1)

[Chemical formula 5]

(2)

[Chemical formula 6]

(3)

R¹, R², and R³ in Formulas (1) to (3) each independently represent a divalent organic group, and m and n each independently represent an integer of 2 to 5000.

These structural units will be individually described below.

[I-1. Structural Unit (1): Polyether Block]

The structural unit (1) is a polyether block composed of structural units represented by —R¹—O— (optionally referred to as ether unit).

In Formula (1), m is an integer indicating the number of the repeating structural units each represented by —R¹—O— (ether unit). It is generally 2 or more, preferably 10 or more, and generally 5000 or less, preferably 1000 or less.

R¹ in Formula (1) represents a divalent organic group.

Preferred divalent organic groups are divalent hydrocarbon groups.

The divalent hydrocarbon group may be an aliphatic hydrocarbon group, an aromatic hydrocarbon group, or a hydrocarbon group comprising an aliphatic hydrocarbons group combined with an aromatic hydrocarbon group (a semiaromatic hydrocarbon group), and preferred is an aliphatic hydrocarbon group.

The aliphatic hydrocarbon group may be linear, branched, cyclic, or any combination of these forms.

The number of carbon atoms in R¹ is generally 1 or more, preferably 2 or more, and generally 6 or less, preferably 4 or less.

Among these preferred R¹ is a divalent aliphatic hydrocarbon group. Examples of the divalent aliphatic hydrocarbon group include a methylene group, an ethylene group, a propylene group, a butylene group, a pentylene group, a hexylene group, an octylene group, and a trimethylene group. Among these preferred are an ethylene group, a propylene group, a trimethylene group, and a butylene group, and more preferred are a 1,2-ethylene group and a 1,2-propylene group, and most preferred is a 1,2-ethylene group. When R¹ is a 1,2-ethylene group, the structural unit represented by —R¹—O— is an ethylene glycol unit (ethylene oxide unit). When R¹ is a 1,2-propylene group, the structural unit represented by —R¹—O— is a propylene glycol unit (propylene oxide unit).

The m $R^1$s (where m represents the number of $R^1$s) may be the same or different. In other words, the structural units represented by Formula (1) may be composed of only one type of $R^1$ or two or more types of $R^1$s in any combination at any ratio. Different types of $R^1$s (that is, different types of ether units) may be present at random or in the form of blocks for every type.

Examples of the particularly preferred structural unit represented by Formula (1) (polyether block) include a poly(ethylene glycol) block (that is, a structural unit composed of an ethylene glycol unit), a poly(propylene glycol) block (that is, a structural unit composed of a propylene glycol unit), and a poly(ethylene glycol)-poly(propylene glycol) block (that is, a structural unit comprising a block composed of an ethylene glycol unit combined with a block composed of a propylene glycol unit). Among these preferred is a poly(ethylene glycol) block.

In addition, examples of the preferred polyether block include a structural unit formed by copolymerization of ethylene glycol units and/or propylene glycol units with one or more other ether units. In this case, the ratio of the total number of the ethylene glycol units and/or the propylene glycol units to m (number of repetitions) of the polyether block is generally 50% or more, and preferably 70% or more.

The structural unit (1) may have any substituent within the intended scope of the present invention.

[I-2. Structural Unit (2): Polyester Block]

The structural unit (2) is a polyester block composed of structural units represented by —CO—$R^2$—O— (optionally referred to as ester unit).

In Formula (2), n is an integer indicating the number of the repeating structural units each represented by —CO—$R^2$—O— (ester unit). It is generally 2 or more, preferably 20 or more, and generally 5000 or less, preferably 1000 or less.

$R^2$ in Formula (2) represents a divalent organic group.

Preferred divalent organic groups are divalent hydrocarbon groups.

The divalent hydrocarbon group may be an aliphatic hydrocarbon group, an aromatic hydrocarbon group, or a hydrocarbon group comprising an aliphatic hydrocarbon group combined with an aromatic hydrocarbon group (a semiaromatic hydrocarbon group), and preferred is an aliphatic hydrocarbon group.

The aliphatic hydrocarbon group may be linear, branched, cyclic, or any combination of these forms.

The number of carbon atoms in $R^2$ is generally 1 or more, preferably 2 or more, and generally 10 or less, preferably 5 or less.

Among these preferred $R^2$ are a divalent aliphatic hydrocarbon group, and/or an ester of an aliphatic carboxylic acid and an aliphatic alcohol. Examples of the divalent aliphatic hydrocarbon group include a methylene group, an ethylene group, a propylene group, a butylene group, a pentylene group, a hexylene group, an ethylidene group, and a trimethylene group. Among these preferred are a methylene group (equivalent to a glycolic acid unit), an ethylidene group (equivalent to a lactic acid unit), a propylene group, an ethylidene group, and a pentylene group (equivalent to a caprolactone unit), and more preferred are a methylene group and an ethylidene group. When $R^2$ is a methylene group, the structural unit represented by —CO—$R^2$—O— is a unit derived from glycolic acid (glycolic acid unit). When $R^2$ is an ethylidene group, the structural unit represented by —CO—$R^2$—O— is a unit derived from lactic acid (lactic acid unit). When $R^2$ is a pentylene group, the structural unit represented by —CO—$R^2$—O— is a unit derived from caprolactone (caprolactone unit). Examples of the lactic acid unit include a unit derived from L-lactic acid (L-lactic acid unit) and a unit derived from R-lactic acid (R-lactic acid unit), and preferred is the L-lactic acid unit.

When $R^2$ is an ester of an aliphatic carboxylic acid and an aliphatic alcohol, $R^2$ is represented by —$R^4$—CO—O—$R^5$—. In this case, examples of $R^4$ include a methylene group, an ethylene group, a propylene group, a butylene group, a pentylene group, a hexylene group, an ethylidene group, and a trimethylene group. Among these preferred are an ethylene group, a trimethylene group, and a butylene group. Examples of $R^5$ include a methylene group, an ethylene group, a propylene group, a butylene group, a pentylene group, a hexylene group, an ethylidene group, and a trimethylene group. Among these preferred are an ethylene group, a propylene group, a butylene group, and a pentylene group, and more preferred is an ethylene group.

The n $R^2$s (where n represents the number of $R^2$s) may be the same or different. In other words, the structural units represented by Formula (2) may be composed of only one type of $R^2$ or two or more types of $R^2$s in any combination at any ratio. Different types of $R^2$s (that is, different types of ester units) may be present at random or in the form of blocks for every type.

Examples of the particularly preferred structural unit represented by Formula (2) (polyester block) include a poly(lactic acid) block (that is, a structural unit formed by polymerization of lactic acid units).

Another example of the preferred polyester block is a structural unit formed by copolymerization of lactic acid units with one or more types of other ester units. In this case, the ratio of the number of the lactic acid units to n (number of repetitions) of the polyester block is generally 40% or more, preferably 60% or more.

The structural unit (2) may also have any substituent within the intended scope of the present invention.

[I-3. Structural Unit (3): Dicarboxylic Acid Unit]

The structural unit (3) represented by —CO—$R^3$—CO— is a dicarboxylic acid unit.

$R^3$ in Formula (3) represents a divalent organic group.

Preferred divalent organic groups are divalent hydrocarbon groups.

The divalent hydrocarbon group may be an aliphatic hydrocarbon group, an aromatic hydrocarbon group, or a hydrocarbon group comprising an aliphatic hydrocarbon group combined with an aromatic hydrocarbon group (a semiaromatic hydrocarbon group), and preferred is an aliphatic hydrocarbon group.

The aliphatic hydrocarbon group may be linear, branched, cyclic, or any combination of these forms.

The number of carbon atoms in $R^3$ is generally 1 or more, preferably 2 or more, and generally 18 or less, preferably 10 or less.

Among these preferred $R^3$ is a divalent aliphatic hydrocarbon group. Examples of the divalent aliphatic hydrocarbon group include a methylene group, an ethylene group, a propylene group, a butylene group, a pentylene group, a hexylene group, an octylene group, a 1,4-cyclohexylene group, a decanylene group, and a dodecanylene group. Among these preferred are an ethylene group, a butylene group, and a decanylene group, and more preferred is a 1,10-decanylene group.

The structural unit (3) may also have any substituent within the intended scope of the present invention.

[I-4. Multiblock Copolymer]

Each number of the structural units (1) to (3) in the copolymer of the present invention should be 2 or more as a lower limit. On the other hand, the upper limits of the numbers are not particularly limited, and depend on the structure of the structural units (1) to (3) and the upper limit of the molecular weight described below.

The numbers of the structural units (1) to (3) may be the same or different.

In addition, for each of the structural units (1) to (3), a plurality of types may be present as described above, and these may be the same or different.

Moreover, the structural units (1) to (3) may be combined with each other in any order.

The copolymer of the present invention is prepared according to the methods described in, for example, [I-5. Method for preparation of multiblock copolymer] and [Examples] in this application, and Japanese Unexamined Patent Application Publication No. 11-255873. The copolymer of the present invention prepared according to these methods can have two or more blocks of each structural unit (1) to (3) (that is, "multiblock copolymer").

The definition of "multiblock copolymer" is based on the description in, for example, "Journal of Japanese Society for Biomaterials", Vol. 21, 2003, January, No. 1, p. 37.

It is preferred that the copolymer of the present invention (multiblock copolymer) substantially contains no chain extender such as a diisocyanate compound.

The content of the structural unit (1) in the copolymer of the present invention is generally 5% by weight or more, preferably 6% by weight or more, more preferably 8% by weight or more, and generally 80% by weight or less, preferably 60% by weight or less, more preferably 50% by weight or less, most preferably 40% or less. A lower content of the structural unit (1) may lead to poor flexibility and expandability and a decreased blood anticoagulant effect. On the other hand, a higher content of the unit may cause the product to be water-soluble, leading to a decreased blood anticoagulant effect and poor dimensional stability due to water absorption.

The content of the structural unit (2) in the copolymer of the present invention is generally 20% by weight or more, preferably 40% by weight or more, more preferably 50% by weight or more, most preferably 60% or more, and generally 95% by weight or less, preferably 94% by weight or less, more preferably 92% by weight or less. A lower content of the structural unit (2) may cause products to be water-soluble which preclude keeping the form of the material, and lead to a significantly high drug-release rate, resulting in undurable products. On the other hand, a higher content of the unit may lead to poor dimensional stability due to water absorption, a decreased blood anticoagulant effect, a significantly low drug-release rate, and poor expandability.

The content of the structural unit (3) in the copolymer of the present invention is generally 0.01% by weight or more, preferably 0.05% by weight or more, more preferably 0.1% by weight or more, and generally 20% by weight or less, preferably 10% by weight or less, more preferably 1% by weight or less. The molar number of the structural unit (3) used is substantially equivalent to that of the structural unit (1). A lower or higher content of the structural unit (3) may preclude an increase in the molecular weight of the copolymer.

Since the content of the structural unit (3) is generally far smaller than the content of the structural unit (1), the total content of the structural unit (1) and the structural unit (3) in the copolymer of the present invention is within the range of the structural unit (1) as described above, that is, generally 5% by weight or more, preferably 6% by weight or more, more preferably 8% by weight or more, and generally 80% by weight or less, preferably 60% by weight or less, more preferably 50% by weight or less, most preferably 40% by weight or less.

The copolymer of the present invention may have another structural unit (hereinafter referred to as "the structural unit (4)") other than the structural units (1) to (3). The type of the structural unit (4) is not particularly limited within the scope of the present invention. The content of the structural unit (4) in the copolymer of the present invention is generally 10% by weight or less, preferably 5% by weight or less, more preferably 1% by weight or less. A higher content of the structural unit (4) may impair the safety to living bodies and lead to poor physical properties.

The content of each structural unit in the copolymer can be determined from a $^1$H-NMR (nuclear magnetic resonance) spectrum measured with the copolymer.

The number average molecular weight of the copolymer of the present invention is generally 10000 or more, preferably 20000 or more, more preferably 30000 or more, and generally 200000 or less, preferably 100000 or less, more preferably 80000 or less. The weight-average molecular weight of the copolymer of the present invention is generally 12000 or more, preferably 24000 or more, more preferably 36000 or more, and generally 400000 or less, preferably 200000 or less, more preferably 160000 or less. A lower molecular weight of the copolymer may lead to accelerated biodegradation and poor mechanical strength. On the other hand, a higher molecular weight may lead to difficulty in processing such as coating. The number average molecular weight and the weight-average molecular weight of the copolymer can be determined by gel permeation chromatography (GPC).

[I-5. Method for Preparation of Multiblock Copolymer]

Methods for the preparation of copolymer of the present invention are not particularly limited. It is generally prepared by polymerization reaction of materials for the structural units (1) to (3).

Examples of the material for the structural unit (1) include monomers generating the structural unit represented by —$R^1$—O— (ether unit) (e.g., glycols such as ethylene oxide, ethylene glycol, propylene oxide, propylene glycol, 1,3-propanediol, 1,4-butanediol, and tetrahydrofuran; and cyclic ethers), and oligomers and polymers derived from these monomers.

Examples of the material for the structural unit (2) include monomers generating the structural unit represented by —CO—$R^2$—O— (ester unit) (e.g., alpha-hydroxylic acids such as glycolic acid, lactic acid, and caprolactone; and cyclic esters), and oligomers and polymers derived from these monomers.

Examples of the material for the structural unit (3) include dicarboxylic acids generating the structural unit represented by —CO—$R^3$—CO— (dicarboxylic acid unit) (e.g., 1,10-decanedicarboxylic acid, succinic acid, and adipic acid).

The materials used for these structural units (1) to (3) and the amounts of the materials may be appropriately selected depending on the composition of the copolymer of the present invention to be prepared.

In addition to the materials for the structural units (1) to (3), any other material (a material for the structural unit (4)) may be optionally used in combination.

The materials for the structural units (1) to (4) may be used alone or in combination at any ratio of two or more.

The polymerization reaction is preferably conducted in the presence of a catalyst.

Examples of the catalyst include metallic tin such as tin powder and tin compounds such as stannous octoate, tin oxide, tin chloride, and tin lactate; metallic zinc such as zinc powder and zinc compounds such as zinc oxide and zinc sulfate; and metallic aluminum and aluminum compounds such as aluminum oxide, aluminum chloride, and aluminum sulfate. These catalysts may be used alone or in combination at any ratio of two or more. Among these preferred are tin compounds, specifically stannous octoate.

The amount of the catalyst used is not particularly limited, but is generally 0.00001% by weight or more, preferably 0.0001% by weight or more, more preferably 0.001% by weight or more, and generally 10% by weight or less, preferably 5% by weight or less, more preferably 1% by weight or less based on the total feeding amount (total amount of the materials, the catalyst, and the solvent). A lower catalyst content may lead to a low-rate reaction, whereas a higher catalyst content may cause safety problems or excess load to a purification process.

The polymerization reaction is preferably conducted in the presence of solvent.

Any solvent that can dissolve or disperse the materials and catalysts described above can be employed. Examples of such solvents include ether solvents such as diphenyl ether, dibutyl ether, and anisole; hydrocarbon solvents such as toluene, xylene, and decalin; ketone solvents such as 3-hexanone, acetophenone, and benzophenone; and ester solvents such as methyl benzoate, monomethyl phthalate, and monoethyl phthalate. These solvents may be used alone or in combination at any ratio of two or more. Among them preferred are diphenyl ether and toluene, specifically diphenyl ether.

While the content of solvents used is not particularly limited, it is generally 25% by weight or more, preferably 30% by weight or more, more preferably 40% by weight or more, and generally 90% by weight or less, preferably 80% by weight or less, more preferably 70% by weight or less based on the total amount of the materials. A lower solvent content may preclude stirring due to high viscosity of the reaction solution, whereas a higher content may lead to a low-rate reaction.

The polymerization reaction is generally conducted batchwise.

Generally, the materials, catalyst, and solvent described above are mixed in a reactor for the polymerization. The mixing may be conducted in any order.

In the case of polycondensation reaction, the reaction is conducted while condensation water is removed from the reaction system.

The reaction temperature is generally 130° C. or higher, preferably 150° C. or higher, and generally 220° C. or lower, preferably 200° C. or lower. A lower reaction temperature may lead to a low-rate reaction, whereas a higher temperature may lead to decreased yield.

The reaction pressure is generally 50 Pa or higher, preferably 100 Pa or higher, and generally 0.1 MPa or lower, preferably 0.01 MPa or lower. A lower reaction pressure may lead to formation of cyclic byproducts in large amounts, whereas a higher pressure may lead to a low-rate reaction.

The reaction atmosphere is not particularly limited, but the reaction is generally conducted under an inert gas atmosphere or an inert atmosphere such as a vacuum condition.

Optionally, stirring can also be conducted during the reaction.

The reaction time varies depending on the reaction temperature and pressure, but is generally 1 hour or longer, preferably 4 hours or longer, and generally 100 hours or shorter, preferably 50 hours or shorter. A shorter reaction time may preclude controlled reaction, whereas a longer reaction time may cause coloring.

Whether polymerization reaction reaches the end point can be confirmed by, for example, measurement of viscosity of the reaction solution and the amount of effluent.

The copolymer of the present invention formed by the polymerization reaction described above can be applied, as it is, to the blood anticoagulant material of the present invention, but may be optionally subjected to post-treatment, for example, purification. Purification can be achieved by, for example, precipitation or use of ion-exchange resins.

[II. Blood Anticoagulant Material]

The blood anticoagulant material of the present invention comprises at least the copolymer of the present invention. The copolymers of the present invention may be used alone or in combination at any ratio of two or more.

The blood anticoagulant material of the present invention may be composed of only the copolymer of the present invention, but may also contain one or more other components. The other components are not particularly limited and can be appropriately selected depending on their intended use and application described below.

The blood anticoagulant material of the present invention can be used in any form.

Specifically, the blood anticoagulant material of the present invention can be formed into any shape to provide a shaped product suitable for its application. Any known shaping process and shape can be employed.

Alternatively, the blood anticoagulant material of the present invention can be used as a coating material (the coating material of the present invention) to coat surfaces of other devices. Any known device can be coated with the coating material of the present invention by any coating technique.

The blood anticoagulant material of the present invention has both high expandability (for example, excellent initial modulus of elasticity and elongation at break) and a blood anticoagulant effect.

In addition, the blood anticoagulant material of the present invention has high safety to living bodies since it has no component having undesired influences on living bodies.

Furthermore, the blood anticoagulant material of the present invention can be used in combination with drugs having a blood anticoagulant effect.

Moreover, characteristics such as biodegradability and controlled-release of drugs can be obtained depending on materials selected.

In view of the effects described above, the blood anticoagulant material of the present invention can be applied to various cases requiring a blood anticoagulant effect.

In particular, the blood anticoagulant material of the present invention is preferably used in order to prevent blood coagulation while various indwelling devices described below are indwelled in living bodies.

[III. Indwelling Device]

The indwelling device of the present invention is composed of the blood anticoagulant material of the present invention described above. Specific examples of the indwelling device include the following two embodiments.

(i) An indwelling device of which a surface is coated with the blood anticoagulant material of the present invention (hereinafter referred to as "the indwelling device of the present invention (i)").

(ii) An indwelling device which itself is composed of the blood anticoagulant material of the present invention (hereinafter referred to as "the indwelling device of the present invention (ii)").

The "indwelling device" herein refers to a device indwelled in contact with blood in or on bodies of various living organisms including human beings as described above.

Examples of the indwelling device include stents, catheters, balloons, vascular prostheses, artificial blood vessels, artificial skins, transdermal devices, adhesion-preventing materials, and wound dressings.

Among these preferred indwelling devices of the present invention are stents. The indwelling devices of the present invention (i) and (ii) will be described below referring to stents as such examples.

One embodiment of the stent of the indwelling device of the present invention (i) (optionally referred to as "the stent (i)") is composed of a stent body (device body) and a coating layer formed by coating a surface of the stent body with the blood anticoagulant material of the present invention as a coating material.

The material, the shape, and the size of the stent are not particularly limited as long as it can be indwelled on lesions of lumens such as blood vessels, bile ducts, tracheas, esophagi, alimentary canal, ureters, and urethras in living bodies, and has mechanical strength enough to endure expanding operation when indwelled in the lumens.

Specifically, the material forming the stent body may be appropriately selected from materials having mechanical strength enough to endure expanding operation when indwelled in the lumens, according to its applied site. Examples of the material include metals, ceramics, and resins. In particular, making the stent body from metals can ensure dwelling of the stent on lesions, since metals have excellent mechanical strength.

Examples of the metals include stainless steel, nickel-titanium alloys, tantalum, nickel, chromium, iridium, tungsten, and cobalt alloys. Particularly preferred stainless steel is SUS316L having high corrosion resistance.

Most of stent bodies made of metals can be expanded with balloons. In addition, stent bodies made of so-called pseudoelastic metals, for example, nickel-titanium alloys that have high strain under constant stress or gradually increased strain with increased stress can self-expand. Accordingly, releasing the compression applied in advance of stent bodies on lesions allows them to self-expand due to their elastic force.

The shape of the stent body is not particularly limited as long as it has mechanical strength enough to be stably indwelled on lumens in living bodies. For example, the stent body may preferably be coiled, cylindrical, mesh cylindrical, or porous cylindrical.

The size of the stent body may be appropriately selected according to its applied site. For example, when the stent is used in cardiac coronary arteries, the outer diameter of the stent body before expanding is generally 0.5 mm or more, preferably 1 mm or more, and generally 10 mm or less, preferably 3 mm or less. The length of the stent body is generally 1 mm or more, preferably 5 mm or more, and generally 100 mm or less, preferably 50 mm or less.

A surface of this stent body is coated with the blood anticoagulant material of the present invention as a coating material to form a coating layer. The coating layer is preferably formed on at least a part of the surface of the stent body, but more preferably on its entire surface.

Coating techniques are not particularly limited. For example, the blood anticoagulant material of the present invention may dissolved or dispersed in an appropriate solvent to prepare a coating solution, which is applied onto a surface of the stent body, and then the solvent is removed by, for example, drying. Alternatively, the blood anticoagulant material of the present invention may be shaped into fibers which are bonded to a surface of the stent body.

The thickness of the coating layer varies depending on application and is not particularly limited, and it is generally 0.01 μm or more, preferably 0.1 μm or more, and generally 2 mm or less, preferably 1 mm or less according to a general standard.

In addition, two or more coating layers may be provided using two or more blood anticoagulant materials of the present invention or using the blood anticoagulant material of the present invention in combination with other materials. In this case, however, the surface layer (that is, a layer in contact with blood in use) of the stent is preferably formed from the blood anticoagulant material of the present invention.

On the other hand, in another embodiment of the stent of the indwelling device of the present invention (ii) (hereinafter optionally referred to as "the stent (ii)"), the stent body (device body) is composed of the blood anticoagulant material of the present invention.

Similarly to the stent (i), the material, the shape, and the size of the stent body are also not particularly limited as long as the stent body of the stent (ii) can be indwelled on lesions of lumens such as blood vessels, bile ducts, tracheas, esophagi, and urethras in living bodies and has mechanical strength enough to endure expanding operation when indwelled in the lumens.

Specifically, the material used for the stent body is the blood anticoagulant material of the present invention. The blood anticoagulant materials of the present invention can be used alone, but are preferably used with one or more other resins in any combination at any ratio in view of mechanical strength. The type of other resin is not particularly limited, and any known resin can be optionally selected in view of application of the stent. In order to ensure the blood anticoagulant effect by the blood anticoagulant material of the present invention, the blood anticoagulant material of the present invention is generally 10% by weight or more, preferably 20% by weight or more in the material for the stent body.

The details such as the shape and the size of the stent body are the same as the stent (i).

The stent body having a plurality of layers or being made of different materials for parts can be formed using two or more different materials. In this case, however, the surface layer (that is, a layer in contact with blood in use) of the stent is preferably formed from the blood anticoagulant material of the present invention.

The stents (i) and (ii) configured as described above are indwelled on lesions of lumens such as blood vessels, bile ducts, tracheas, esophagi, alimentary canal, ureters, and urethras in living bodies. The stents can be indwelled by, for example, balloon dilatation. If the stent body is elastic, the self-expandability due to its elastic force can also be utilized.

It is also possible to fix drugs to the outermost surfaces of the stent (i) and (ii) (the surface of the coating layer in the case of stent (i) and the surface of the stent body in the case of the stent (ii)) and to have them controlled-released in living bodies. Examples of the drug to be fixed include biologically active substances. Note that the biologically active substances refer to a single substance or a compound group that is physiologically or pharmacologically active in living organisms regardless of whether it is derived from living bodies or is a synthetic substance. Another example of the drug is so-called prodrug that is metabolized into an active form in living bodies.

Examples of the preferred biologically active substance include substances that can prevent restenosis while stents are indwelled on lesions of lumens. The type of biologically active substance is not particularly limited. Examples of the biologically active substance include anticancer agents such as antineoplastic antibiotics, alkaloidal drugs, alkylating agents, antimetabolites, tyrosine kinasease inhibitors, and DNA synthesis inhibitors; depressors such as ACE inhibitors, calcium antagonists, beta-adrenergic antagonists, alpha-adrenergic antagonists, alpha/beta-adrenergic antagonists, angiotensin II antagonists & inhibitors, and diuretic hypotensors; immunosuppressant agents; antirheumatic drugs; antihyperlipidemic agents such as HMG-CoA reductase inhibitors, probucol, and lipid-modifying agents; antiarteriosclerotic drugs such as vascular smooth muscle cell growth inhibitors, integrin inhibitors, and prostaglandin derivatives; antithrombotic agents such as antiplatelet agents and thrombolytic agents; antibiotics; antiallergic agents; antiinflammatory agents; NO production accelerators; antioxidants such as flavonoid, carotenoid, and catechins; and biological substances such as cytokine, hormone, and lymphokine.

Examples of the preferred antineoplastic antibiotics as the anticancer agents include mitomycin C, doxorubicin hydrochloride, actinomycin D, daunorubicin hydrochloride, idarubicin hydrochloride, pirarubicine hydrochloride, aclarubicin hydrochloride, epirubicin hydrochloride, peplomycin hydrochloride, and zinostatin stimalamer.

Examples of the preferred alkaloidal drugs as the anticancer agents include vincristine sulfate, vinblastine sulfate, vindesine sulfate, irinotecan sulfate, paclitaxel, and docetaxel hydrate.

Examples of the preferred alkylating agents as the anticancer agents include cyclophosphamide.

Examples of the preferred antimetabolites as the anticancer agents include methotrexate.

Examples of the preferred tyrosine kinase inhibitors as the anticancer agents include genistein, tyrphostin, and erbstatin.

Examples of the preferred ACE inhibitors as the depressors include quinapril hydrochloride, perindopril erbumine, trandolapril cilazapril, temocapril hydrochloride, delapril hydrochloride, enalapril maleate, lisinopril, and captopril.

Examples of the preferred calcium antagonists as the depressors include, nifedipine nilvadipine, diltiazem hydrochloride, benidipine hydrochloride, and nisoldipine.

Examples of the preferred immunosuppressant agents include sirolimus, tacrolimus hydrate, azathioprine, cyclosporin, mycophenolate mofetil, gusperimus hydrochloride, and mizoribine.

Examples of the preferred antirheumatic drugs include gold sodium thiomalate, penicillamine, and lobenzarit disodium.

Examples of the preferred HMG-CoA reductase inhibitors as the antihyperlipidemic agents include cerivastatin sodium, atorvastatin, nisvastatin, pitavastatin, fluvastatin sodium, simvastatin, lovastatin, and pravastatin sodium.

Examples of the preferred antithrombotic agents include antiplatelet agents, thrombolytic agents, heparin, ticlopidine hydrochloride, and hirudin. Examples of the preferred antiplatelet agents include GP IIb/IIIa antagonists.

Examples of the preferred antiallergic agents include tranilast.

Examples of the preferred antiinflammatory agents include steroids such as dexamethasone and prednisolone; and aspirin.

Examples of the preferred carotenoids as the antioxidants include retinoids, anthocyanins, proanthocyanidins, lycopene, and beta-carotene. Examples of the preferred retinoids include all-trans retinoic acid.

Examples of the preferred catechins as the antioxidants include epicatechin gallate.

Examples of the preferred cytokines as the biological substances include interferon, epidermal growth factor (EGF), vascular endothelial growth factor (VEGF), hepatocyte growth factor (HGF), platelet derived growth factor (PDGF), and basic fibrolast growth factor (bFGF).

These biologically active substances may be used alone or in combination at any ratio of two or more.

Methods of fixing biologically active substances to the outermost surface of the stent are not particularly limited. For example, the biologically active substances may be melted and applied onto the outermost surface of the stent. Alternatively, the biologically active substances may be dissolved in a solvent to prepare a solution, in which the stent is immersed and then took out to remove the solvent by transpiration or any other means. Alternatively, the solution may be sprayed over the outermost surface of the stent, and the solvent is removed by transpiration or any other means.

The thickness of the biologically active substance fixed to the outermost surface of the stent are determined within the range in which the performance of the stent body such as accessibility (delivery property) to lesions, irritation to blood vessel walls, and a blood anticoagulant effect can be maintained, and the effect of the biologically active substances can be obtained. Specifically, it is generally 0.2 µm or more, preferably 1 µm or more, and generally 100 µm or less, preferably 50 µm or less, more preferably 10 µm or less.

The stents (i) and (ii) have been described above as an example of the indwelling device of the present invention. But the indwelling device of the present invention is not limited to these stents (i) and (ii), and various embodiments of the present invention can be implemented within the scope of the present invention.

[IV. Medical Device and Treatment Using the Device]

The treatment of the present invention uses a medical device composed of the blood anticoagulant material of the present invention. Examples of such medical devices include not only the indwelling device described above, but also other devices that are not indwelled in living bodies. In particular, the blood anticoagulant material of the present invention is preferably applied to medical devices of which parts come into contact with blood. Examples of such devices include artificial heart lung machines, dialysis machines, and surgical devices.

Examples of the treatment using the medical device composed of the blood anticoagulant material of the present invention include treatment of angina pectoris. In such treatment, a stent coated with the blood anticoagulant material of the present invention is inserted into blood vessels from, for example, a groin, a wrist, and an elbow. And then, the stent is moved to narrowed sites of, for example, cardiac coronary arteries, and expanded with, for example, a balloon to dilate the blood vessels.

EXAMPLES

The present invention will now be described in more detail by reference to the following examples, but it is not limited to these examples without departing from the spirit of the present invention.

Note that the term "parts" represents "parts by weight" throughout the following description unless otherwise specified. In addition, the term "wt %" represents "% by weight".

[Blood Coagulation Test]

Blood coagulation tests for each of Example and Comparative Example described below were performed according to the following two methods.

Blood Coagulation Test (1) (Example 1 and Comparative Examples 1 and 2)

The start point was when blood was drawn into a dry sterile syringe by puncture of an antecubital vein in a rat. About 2.5 mL of blood was collected, and 1 mL of which was taken into each of two small test tubes kept in a thermostat bath at 37° C. The tube containing the blood was allowed to stand in the thermostat bath at 37° C. After three minutes, one of the test tubes was inclined every 30 seconds to observe the blood flow. After the blood flow stopped due to blood coagulation, the same procedure was repeated with the other test tube. The test was terminated when the blood flow stopped in the other test tube to observe the blood coagulation in the test tube.

Blood Coagulation Test (2) (Examples 1, 2, and 3, and Comparative Example 1)

A sample (10 mm in diameter, 70 μm in thickness) was immersed in bovine preserved blood containing 50 mM of calcium chloride. The sample was collected after a period of time (30 minutes, 1, 3, 6, 12, or 24 hours) to observe appearance of the sample. Through glutaraldehyde immobilization, alcohol dehydration, and lyophilization from tert-butyl alcohol, the sample was observed with a SEM. The results are shown on the column "blood anticoagulant effect" in Table 1. FIGS. 1 to 8 are representative photographs showing the appearance of the sample and the SEM observation.

Figure 1:
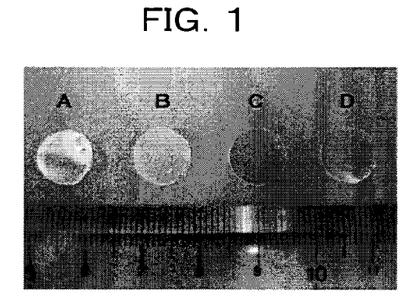
FIG. 1 is a photograph, instead of a drawing, showing the results of Examples or Comparative Example of the present invention.
Figure 2:
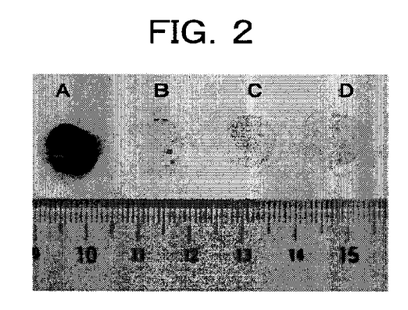
FIG. 2 is a photograph, instead of a drawing, showing the results of Examples or Comparative Example of the present invention.
Figure 3:
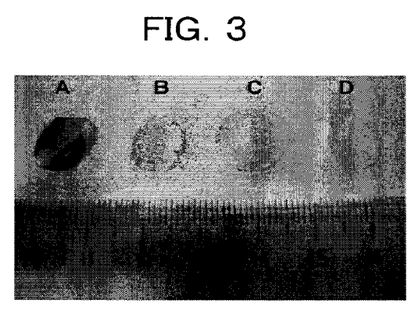
FIG. 3 is a photograph, instead of a drawing, showing the results of Examples or Comparative Example of the present invention.
Figure 4:
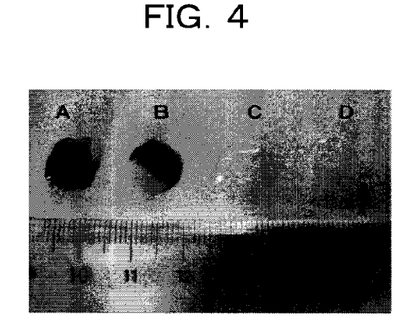
FIG. 4 is a photograph, instead of a drawing, showing the results of Examples or Comparative Example of the present invention.

FIGS. 1 to 4 are photographs showing the appearance of blood in the blood coagulation test (2). FIG. 1 shows untested samples in which Sample A was obtained from Comparative Example 1, Sample B from Example 3, Sample C from Example 1, and Sample D from Example 2. FIG. 2 shows samples after 0.5 hours from the start of the test in which A was obtained from Comparative Example 1, B from Example 3, C from Example 1, and D from Example 2. FIG. 3 shows samples after 12 hours from the start of the test in which A was obtained from Comparative Example 1, B from Example 3, C from Example 1, and D from Example 2. FIG. 4 shows samples after 24 hours from the start of the test in which A was obtained from Comparative Example 1, B from Example 3, C from Example 1, and D from Example 2.

Figure 5:
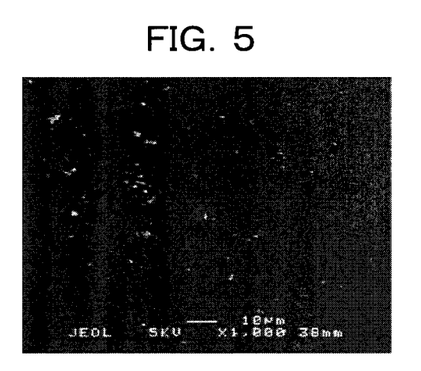
FIG. 5 is a photograph, instead of a drawing, showing the result of Example of the present invention.
Figure 6:
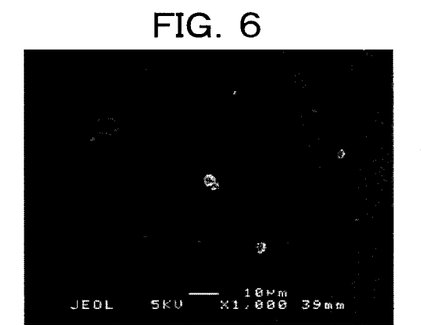
FIG. 6 is a photograph, instead of a drawing, showing the result of Example of the present invention.
Figure 7:
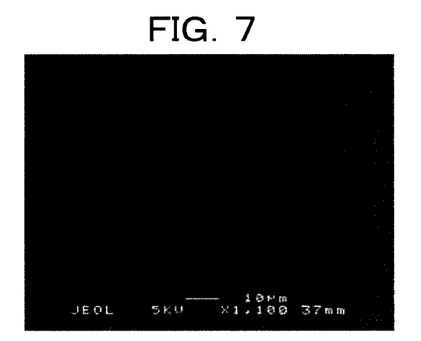
FIG. 7 is a photograph, instead of a drawing, showing the result of Example of the present invention.
Figure 8:
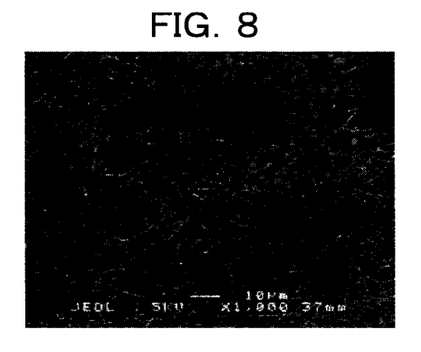
FIG. 8 is a photograph, instead of a drawing, showing the result of Example of the present invention.

FIGS. 5 to 8 are photographs (1,000 to 1,100-fold) obtained from the SEM observation in the blood coagulation test (2). Each photograph shows a sample after 0.5 hours from the start of the test. Specifically, FIG. 5 shows Example 1, FIG. 6 shows Example 2, FIG. 7 shows the parts without blood coagulation in Example 3, and FIG. 8 shows the part with blood coagulation in Example 3.

[Controlled-release Test of Drugs]

Sample Preparation for Controlled-Release Test

Into a glass petri dish having a diameter of 42 mm was placed 2.4 mL of 7.5 wt %-polymer/chloroform solution containing paclitaxel (0.2 mg/mL). The solution was air-dried overnight at ordinary temperature, and was vacuum-dried for 12 hours to form a cast film. The resultant cast film was punched out with a stainless-steel punch having a diameter of 6 mm to prepare a sample for the controlled-release test.

Controlled-release Test

A controlled-release test was carried out with the resultant sample, which was immersed in 10 mL of 0.1 w/v %-Tween80/PBS (phosphate buffer), and incubated under shaking at 37° C.

After a certain period of time, 0.5 mL of solution (measurement sample) was collected, and the same amount (0.5 mg) of 0.1 w/v %-Tween80/PBS was further added to the solution for continuation of incubation.

Measurement of Drug-release Rate

The drug-release rate was measured with an LC-MS (liquid chromatograph mass spectrometer). The system used was LC-10A manufactured by SHIMADZU Corporation, and the column used was Inertsil ODS-3 (2.1×100 mm, 3 um) manufactured by GL Sciences Inc.

The measurement was carried out in the column vessel kept at 40° C. with water/acetonitrile (for HPLC manufactured by Kanto Chemical Co., Inc.)=40/60 as a mobile phase at a flow rate of 0.2 mL/min.

Example 1

Into a flask equipped with a stirrer and a condenser having an oil separator were placed 9 parts of poly(ethylene glycol) (number average molecular weight=2000, manufactured by Wako Pure Chemical Industries, Ltd.), 0.246 parts of 1,10-decanedicarboxylic acid, 21 parts of L-lactic acid oligomer (prepared according to the description in Journal of Polymer Science: Part A, Vol. 37, 1513-1521 (1999)), 0.3 parts of stannous octoate, and 30 parts of diphenyl ether. The resultant mixture was evacuated over 2 hours and polymerized at 1.3 kPa at 180° C. for 40 hours. During the polymerization, cooling water was maintained at 60° C., and condensation water was removed from the reaction system, while the solvent was recycled to the system. The resultant polymerization solution was placed in a large amount of methanol for precipitation. The resultant polymer was purified by repeating dissolution in chloroform and placement into a large amount of methanol, and dried with a hot air dryer to form a white multiblock copolymer.

The yield of the resultant multiblock copolymer was 78%.

The ratio by weight of the poly(ether ester) block (copolymer block of poly(ethylene glycol) and 1,10-decanedicarboxylic acid) to the poly(L-lactic acid) block determined from a $^1$H-NMR spectrum was (poly(ether ester) block)/(poly (L-lactic acid)block)=31/69.

The number average molecular weight and the weight-average molecular weight of this multiblock copolymer by GPC were 35,800 and 59,900, respectively.

Neither the melting point nor glass transition temperature was observed by differential scanning calorimetry (DSC) of this multiblock copolymer.

A cast film having a thickness of 80 μm was formed with a chloroform solution of the resultant multiblock copolymer, and was punched out to prepare samples having a width of 4 mm and a length of 20 mm. These samples were subjected to a tensile test using a tensile tester at a tension rate of 100 mm/min. The results showed that the initial modulus of elasticity was 3.0 MPa, the tensile strength was 2.3 MPa, and the elongation at break was 360%.

In addition, the chloroform solution of the resultant multiblock copolymer was placed into a glass test tube to apply the solution onto the inside of the test tube, and the test tube was dried, whereby the inside of the test tube was coated with the multiblock copolymer. The blood coagulation test (1) was carried out with this test tube according to the procedure described above. Partial coagulation of the blood was observed after 5 minutes from the start of the test.

The blood coagulation test (2) was also carried out according to the procedure described above. The results are shown on the column "Blood anticoagulant effect" in Table 1. FIGS. 1 to 5 are photographs showing the appearance of blood and the SEM observation.

Moreover, the controlled-release test of drugs was carried out according to the procedure described above. The results are shown on the column "Drug-release rate" in Table 1.

Examples 2 and 3

The multiblock copolymer was prepared as in Example 1 except that the ratio of poly(ethylene glycol) (number average molecular weight=2000, manufactured by Wako Pure Chemical Industries, Ltd.), 1,10-decanedicarboxylic acid, and L-lactic acid oligomer was changed as shown in Table 1.

The blood coagulation test (2) was carried out with the resultant multiblock copolymer according to the procedure described above. The results are shown on the column "Blood anticoagulant effect" in Table 1. FIGS. 1 to 4 and FIGS. 6 to 8 are photographs showing the appearance of blood and the SEM observation. FIG. 7 shows the parts without blood coagulation in Example 3 and FIG. 8 shows the parts with blood coagulation in Example 3.

In addition, a controlled-release test of drugs was carried out according to the procedure described above. The results are shown on the column "Drug-release rate" in Table 1.

Comparative Example 1

The polymerization reaction was carried out as in Example 1 except that poly(ethylene glycol) and 1,10-decanedicarboxylic acid were not used, whereby poly(L-lactic acid) was produced.

The tensile test was carried out with poly(L-lactic acid) (number average molecular weight Mn=100200, weight-average molecular weight Mw=196000) as in Example 1. The results showed that the initial modulus of elasticity was 530 MPa, the tensile strength was 11 MPa, and the elongation at break was 20%.

The inside of the test tube was coated with this poly(L-lactic acid) and the blood coagulation test was carried out as in Example 1. Partial coagulation of the blood was observed within 5 minutes from the start of the test.

The blood coagulation test (2) was also carried out according to the procedure described above. The results are shown on the column "Blood anticoagulant effect" in Table 1. FIGS. 1 to 4 are photographs showing the appearance of blood and SEM observation.

Moreover, the controlled-release test of drugs was carried out according to the procedure described above. The results are shown on the column "Drug-release rate" in Table 1.

Comparative Example 2

The blood coagulation test (1) was carried out with an uncoated glass test tube as in Example 1. The blood completely coagulated within 3 minutes from the start of the test.

Comparative Example 3

Into a glass polymerization tube equipped with a stirring blade, a nitrogen inlet, and a vacuum port were placed 70.0 parts of lactic acid oligomer (manufactured by Musashino Chemical Laboratory, Ltd.), 30.0 parts of poly(ethylene glycol) 4000 (manufactured by Wako Pure Chemical Industries, Ltd.), 2.302 parts of dodecanedicarboxylic acid (manufactured by Wako Pure Chemical Industries, Ltd.), and 0.20 parts of stannous octoate (manufactured by Nacalai Tesque, Inc.). After evacuation-nitrogen substitution was repeated three times, the tube was nitrogen-sealed.

This polymerization tube was placed in an oil bath at 180° C. for the reaction for 2 hours. Then, the oil bath was heated to 200° C. over 30 minutes for further reaction at 200° C. for 2 hours. Next, the reaction mixture in the tube was evacuated to 133 Pa or less for 1.5 hours, and the reaction was continued for 12 hours while the produced lactide was removed from the reaction system.

After the reaction, the pressure in the tube was recovered with nitrogen, and the bottom of the tube was broken to drawn out the produced polymer into a strand form. This polymer was dissolved in a 4-fold amount of chloroform, and the resultant solution was transferred in a 10-fold amount of diethyl ether for the precipitation of the polymer.

The resultant polymer was separated by filtration and vacuum-dried at room temperature for 8 hours. The ratio by weight of the poly(ether ester) block to the poly(L-lactic acid) block determined from a $^1$H-NMR spectrum of the resultant multiblock copolymer was 14/86. The number average molecular weight and the weight-average molecular weight of the multiblock copolymer by GPC were 48100 and 71400, respectively.

The tensile test was carried out as in Example 1. The results showed that the initial modulus of elasticity was 1.8 MPa, the tensile strength was 4.9 MPa, and the elongation at break was 380%.

The controlled-release test of drugs was also carried out. The results are shown on the column "Drug-release rate" in Table 1.

[Results]

The results of Examples and Comparative Examples are shown in Table 1 wherein wt % represents % by weight and hr represents hour.

TABLE 1

| | Coating material | Weight-average molecular weight | Initial modulus of elasticity [MPa] | Tensile strength [MPa] | Elongation at break [%] | Blood anticoagulant effect* | Drug-release rate** | | | |
|---|---|---|---|---|---|---|---|---|---|---|
| | | | | | | | 1 [hr] | 3 [hr] | 6 [hr] | 24 [hr] |
| Example 1 | Multiblock copolymer (poly(lactic acid) block/poly(ether ester) block = 69 wt %/31 wt %) | 59,900 | 3.0 | 2.3 | 360 | A | 6% | 17% | 30% | 75% |
| Example 2 | Multiblock copolymer (poly(lactic acid) block/poly(ether ester) block = 58 wt %/42 wt %) | 34,900 | 3.9 | 1.8 | 350 | A | 6% | 13% | 27% | 56% |
| Example 3 | Multiblock copolymer (poly(lactic acid) block/poly(ether ester) | 33,200 | *1 | *1 | *1 | B | 2% | 2% | 2% | 2% |

TABLE 1-continued

| | Coating material | Weight-average molecular weight | Initial modulus of elasticity [MPa] | Tensile strength [MPa] | Elongation at break [%] | Blood anticoagulant effect* | Drug-release rate** | | | |
|---|---|---|---|---|---|---|---|---|---|---|
| | | | | | | | 1 [hr] | 3 [hr] | 6 [hr] | 24 [hr] |
| Comparative Example 1 | block = 97 wt %/3 wt %) Poly(lactic acid) | 196,000 | 530 | 11 | 20 | C | 0% | 0% | 2% | 2% |
| Comparative Example 2 | None | — | — | — | — | C | — | — | — | — |
| Comparative Example 3 | Multiblock copolymer (poly(lactic acid) block/poly(ether ester) block = 14 wt %/86 wt %) | 71,500 | 1.8 | 4.9 | 380 | *2 | 98% | 98% | 100% | — |

*Blood anticoagulant effect: A = high, B = moderate, C = none
**Drug-release rate: the ratio of the amount of eluted drugs to the amount of fed drugs (% by weight)
*1: Not measured due to fragility
*2: Not tested due to dissolution The results in Table 1 show that the multiblock copolymers (the blood anticoagulant materials of the present invention) of Examples 1 to 3 have excellent mechanical properties compared with the poly(lactic acid) of Comparative Example 1.

Furthermore, the results in Table 1 and FIGS. 1 to 8 show that the multiblock copolymers (the blood anticoagulant materials of the present invention) of Examples 1 to 3 have a excellent blood anticoagulant effect compared with the poly (lactic acid).

Moreover, the multiblock copolymer of Example 1 evidently exhibits excellent controlled-release of drugs compared with poly(lactic acid) or a copolymer in which the content of a poly(ether ester) block is more than 50% by weight.

Industrial Applicability

The present invention can be applied to various areas requiring prevention of blood coagulation, and in particular, is preferably used in prevention of blood coagulation while an indwelling device such as a stent composed of a blood anticoagulant material is indwelled in a living body. In addition, the invention can be applied to treatment using a medical device composed of the blood anticoagulant material.

Although the present invention has been described in detail with reference to particular embodiments thereof, it is apparent to those skilled in the art that various modifications can be made thereto without departing from the spirit and scope of the present invention.

The present application is based on JP-A-2006-312167 and JP-A-2007-298711 filed on Nov. 17, 2006, which are herein incorporated in their entireties by reference.

The invention claimed is:

1. A blood anticoagulant material comprising a multiblock copolymer having at least a structural unit represented by Formula (1), a structural unit represented by Formula (2), and a structural unit represented by Formula (3):

Formula (1)]

Formula (2)]

Formula (3)]

wherein, $R^1$, $R^2$, and $R^3$ in Formulas (1) to (3) each independently represent a divalent organic group, and m and n each independently represent an integer of 2 to 5000;

wherein the total content of the structural unit represented by Formula (1) and the structural unit represented by Formula (3) in the multiblock copolymer is 5% to 50% by weight.

2. The blood anticoagulant material according to the claim 1, wherein the total content of the structural unit represented by Formula (2) is 20% to 95% by weight.

3. The blood anticoagulant material according to claim 1, wherein the structural unit represented by Formula (1) is a poly(ethylene glycol) block.

4. The blood anticoagulant material according to claim 1, wherein the structural unit represented by Formula (2) is a structural unit comprising at least one monomeric component selected from a group consisting of lactic acid, glycolic acid, and caprolactone.

5. The blood anticoagulant material according to claim 1, wherein $R^3$ in Formula (3) is a divalent hydrocarbon group having ten or less carbon atoms.

6. A coating material comprising the blood anticoagulant material according to claim 1.

7. An indwelling device of which a surface is coated with the coating material according to claim 6.

8. An indwelling device comprising the blood anticoagulant material according to claim 1.

9. The indwelling device according to claim 7, wherein the indwelling device is a stent.

10. The blood anticoagulant material according to claim 1, wherein the blood anticoagulant material is used in order to prevent blood coagulation while an indwelling device is indwelled in a living body.

11. A medical treatment comprising contacting blood of a subject in need thereof with a medical device comprising the blood anticoagulant material according to claim 1.

12. The indwelling device according to claim 8, wherein the indwelling device is a stent.

13. A blood anticoagulant material, comprising:
a multiblock copolymer having at least a structural unit represented by formula (1), a structural unit represented by formula (2), and a structural unit represented by formula (3):

wherein, $R^1$, $R^2$, and $R^3$ in formulas (1) to (3) each independently represent a divalent organic group, and m and n each independently represent an integer of 2 to 5000;
wherein the total content of the structural unit represented by formula (1) and the structural unit represented by formula (3) in the multiblock copolymer is 5% to 50% by weight, and wherein the multiblock copolymer contains no diisocyanate structural unit.

14. The blood anticoagulant material of claim 13, further comprising at least one selected from the group consisting of an antineoplastic antibiotic, an alkaloidal drug, an alkylating agent, an antimetabolite, a tyrosine kinasease inhibitor, a DNA synthesis inhibitor, an ACE inhibitor, a calcium antagonist, a beta-adrenergic antagonist, an alpha-adrenergic antagonist, an alpha/beta-adrenergic antagonist, an angiotensin II antagonist, an angiotensin II inhibitor, a diuretic hypotensor, an immunosuppressant agent, an antirheumatic drug; an HMG-CoA reductase inhibitor, a probucol, a lipid-modifying agent, a vascular smooth muscle cell growth inhibitor, an integrin inhibitor, a prostaglandin derivative, an antiplatelet agent, a thrombolytic agent, an antibiotic, an antiallergic agent, an antiinflammatory agent, an NO production accelerator, a flavonoid, a carotenoid, a catechin, a cytokine, a hormone, and a lymphokine.

15. A stent coated with the blood anticoagulant material of claim 13.

16. The blood anticoagulant material of claim 1, wherein the total content of the structural unit represented by Formula (1) and the structural unit represented by Formula (3) in the multiblock copolymer is 31% to 50% by weight.

17. The blood anticoagulant material of claim 1, wherein the total content of the structural unit represented by Formula (1) and the structural unit represented by Formula (3) in the multiblock copolymer is 31% to 42% by weight.

18. The blood anticoagulant material of claim 1, wherein the molar number of the structural unit represented by Formula (3) is substantially equivalent to the molar number of the structural unit represented by Formula (1).

19. The blood anticoagulant material of claim 1, wherein the multiblock copolymer has substantially no diisocyanate compound.

* * * * *